United States Patent [19]

Morikawa et al.

[11] 4,241,083
[45] Dec. 23, 1980

[54] GERMICIDAL COMPOSITION FOR AGRICULTURE AND HORTICULTURE

[75] Inventors: Yukiteru Morikawa, Yokohama; Hideo Nishikawa, Ibaraki, both of Japan

[73] Assignee: Nippon Gohsei Kagaku Kogyo Kabushiki Kaisha, Osaka, Japan

[21] Appl. No.: 88,652

[22] Filed: Oct. 26, 1979

[30] Foreign Application Priority Data

Oct. 27, 1978 [JP] Japan ............................ 53-132933
Aug. 25, 1979 [JP] Japan ............................ 54-108387

[51] Int. Cl.³ .................. A01N 37/10; C07C 101/02; C07C 101/30
[52] U.S. Cl. ................................ 424/309; 560/38; 560/39
[58] Field of Search ............... 424/309; 560/38, 39; 562/444

[56] References Cited

FOREIGN PATENT DOCUMENTS 62321 6/1968 German Democratic Rep. ........ 560/38
1485765 6/1967 France ........................................ 560/38

*Primary Examiner*—Douglas W. Robinson
*Attorney, Agent, or Firm*—Wenderoth, Lind & Ponack

[57] ABSTRACT

A germicidal composition which contains 2-(2-hydroxyethylamino)-3-benzoylpropionates or salts thereof as an active ingredient has excellent control effects for the agricultural and horticultural plants diseases, especially for apple canker and the powdery mildews of various plants. Said composition does little damage to the plants and has extremely weak toxicity to man and beast.

7 Claims, No Drawings

GERMICIDAL COMPOSITION FOR AGRICULTURE AND HORTICULTURE

DETAILED DESCRIPTION OF INVENTION

The present invention relates to a novel germicidal composition for agriculture and horticulture, and more particularly relates to agricultural chemicals which are very effective for eliminating apple canker and powdery mildews on various plants.

In the fields of agriculture and horticulture, the damages caused by a variety of disease germs or fungi come into question.

For example, the apple canker most feared in growing apples is caused by *Valsa ceratosperma* and appears as brown and slightly swelled disease spots on the bark of apple tree's trunk and branches from the latter part of March to June. The disease spots spread rapidly in the interval from summer to autumn. Next, black granular dots appear on the surface of the disease spots. The bark of the apple tree becomes fishskined and the tree soon withers. This disease is so contagious that it is impossible to harvest apples once the disease breaks out.

To eliminate apple canker germicides such as Benomyl (methyl 1-(butylcarbamoyl)-2-benzimidazol-carbamate), thiophanate methyl (1,2-bis(3-methylcarbonyl-2-thioureido)) and the like are known and effectively employed. However, after the canker attacks, these germicides can only weakly prevent the progress of the disease, that is, they produce only so-called "dull effects". A germicide which can completely prevent apple canker has not yet been found. Accordingly, there is no often solution for preventing the spread of apple canker except cutting down diseased apple trees.

It has been found that 2-(2-hydroxyethylamino)-3-benzoylpropionates or their salts have superior control abilities for many agricultural and horticultural plant diseases, particularly for apple canker and powdery mildews on various kinds of plants, and cause little damage when applied and are of extremely weak toxicity to man, beast and fish.

The germicidal composition according to the present invention comprises as an active ingredient 2-(2-hydroxyethylamino)-3-benzoylpropionates in the compound formula:

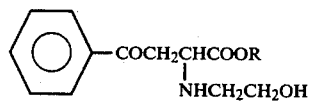

wherein R is alkyl group, or salts thereof.

In the invention's germicidal composition a preferable alkyl group for the above formula is one having from one to four carbon atoms, such as the methyl, ethyl, propyl, isopropyl, or sec-butyl groups. When the alkyl group has more than five carbon atoms, the germicidal effect decreases to an impractical level.

The 2-(2-hydroxyethylamino)-3-benzoylpropionates may be used in the form of optional salts with suitable acids, for example, inorganic acids such as hydrochloric acid, sulphuric acid and the like or organic acids such as acetic acid, oxalic acid, succinic acid, malic acid, malonic acid, adipic acid, sorbic acid, crotonic acid, benzoic acid and the like may be used.

The compounds of the above general formula are easily prepared by, for example, reaction of β-benzoyl acrylate with monoethanol amine.

The invention's germicidal composition for agriculture and horticulture can be used as a water soluble powder, solution, emulsifiable concentrate, wettable powder, aqueous solution, dust, granule, dust-granule, paste or the like. Use of water soluble powder, wettable powder, or dust is particularly preferred.

When the invention's germicidal composition is used as a solution, the less harmful solvents, such as benzene, xylene, naphtha, dimethylnaphthalene and the like are employed. The composition of the present invention may be used by dissolving them in comparatively high hydrophilic solvents, such as alkylene glycols and Cellosolves. However, the compounds should preferably be used in the form of an aqueous solution prepared by neutralization with acids without any organic solvents. The aqueous solution may be prepared as a formulation having 10 to 40 percent by weight of actives. To improve spreadability and wettability, a surfactant may be blended in, and to prevent freezing of the aqueous solution, ethylene glycol and the like may be used in the amount of 5–20% by weight.

The preferable surfactants for use as spreading agents are, for example, nonionic surfactants such as polyoxyethylene alkyl ether, polyoxyethylene alkyl ester, polyoxyethylene alkyl phenyl ether and the like, or anionic surfactants such as alkyl sulfate, alkyl sulfonate, dialkyl sulfosuccinate, alkyl benzene sulfonate and the like. And of course, cationic and amphoteric surfactants may be used. These surfactants may be used in a concentration of about 0.001–0.5%. In order to improve adherability, aqueous thickening agents, such as casein, albumin, glue, polyvinyl alcohol, carboxymethylcellulose, methylcellulose, hydroxyethylcellulose and the like may be blended in.

When the invention's germicidal composition is used as an emulsifiable concentrate the germicidal compound is dissolved with an emulsifying agent in solvents such as xylene, benzene, naphtha, dimethylnaphthalene, isopropanol, n-buthanol and the like. The emulsifiable concentrate may contain 10–50% by weight of the active ingredient. A suitable emulsifying agent is one which self-emulsifies easily when the emulsifiable concentrate is added into water and stabilizes the emulsion during application. Usually, such an emulsifying agent may be selected from the class which consists of nonionic surfactants, such as polyoxyethylene alkylphenyl ether, polyoxyethylene alkyl ether, polyethylene glycol alkyl ester, sorbitan alkyl ester, polyoxyethylene sorbitan alkyl ester and the like, or anionic surfactants, such as alkylbenzene surfonate, alkyl sulfate and the like. The emulsifying agent may be used in the amount of about 2–25% by weight.

The most typical form of the invention's germicidal composition is wettable powder or dust. The unneutralized compounds employed in the present invention are formulated as a wettable powder because they are oily. The neutralized compounds employed in the present invention are formulated as they are because they are powdery. When formulating as a wettable powder, conventional carriers such as clay, kaolin, talc, diatomaceous earth, bentonite, and the like may be used.

Dispersants, for example, anionic surfactants such as naphthalene sulfonate, alkylnaphthalene sulfonate, formalin condensates thereof, alkylbenzene sulfonate, dialkyl sulfosuccinate, alkyl sulfate, lignin sulfonate, fatty acid soap and the like and nonionic surfactants, such as polyoxyethylene alkylphenyl ether, polyoxyethylene alkyl ether, polyethylene glycol alkyl ester, Pluronic, polyoxyethylene alkylamine, polyoxyethylene sorbitan alkylate, sorbitan alkylate and the like and mixture thereof may be used in the wettable powder. And of course, cationic or amphotelic surfactants may be used. In order to improve the self-degradation and suspendability of the wettable powder in water in use and to improve the suspension's spreadability, thickening agents, such as methyl cellulose, hydroxyethyl methyl cellulose, hydroxypropyl methyl cellulose, carboxymethyl cellulose, polyvinyl alcohol, casein, albumin and the like may be blended.

The invention's germicidal composition may be used as granules prepared by mixing the germicide with a suitable powder or by adsorbing the germicide on carrier particles. The germicides may be used as viscous pastes applied to the parts attacked by the disease.

The invention's germicidal composition for agriculture and horticulture is efficacious against such plant diseases as apple canker, powdery mildews on various kinds of plants, verticillium wilt on eggplants, leaf spot on eggplants, sclerotinia rot on eggplants, gray mold on onions, scab on cucumbers, anthracnose on cucumbers, vine blight on cucumbers, leaf mold on tomatoes, ring spot on tomatoes, leaf spot on tomatoes, fusarium wilt on tomatoes, root rot on tomatoes, late blight on tomatoes, anthracnose on watermelons, chestnut blight, mulberry blight (die-back), brown rust (leaf rust) on wheat, purple speck on soybeans, pear rust, black spot on pears and the like.

The invention's germicidal composition is especially effective for combating apple canker and powdery mildews (p.m.) of various kinds of plants, e.g., p.m. of tomatoes, eggplants, radishes, sesames, calza and the like, caused by *Erysiphe cichoracearum;* p.m. of tomatoes, eggplants, cucumbers, pimentos and the like caused by *Leveillula taurica;* p.m. of cucumbers, pumpkins, watermelons, melons (including *Cucumis melo* var. Makuwa), sunflowers and the like caused by *Sphaerotheca fuliginea;* p.m. of strawberries, hops, trefoils and the like caused by *Sphaerotheca humuli;* p.m. of peas, tomatoes, tobacco plants and the like caused by *Microsphaera poligoni;* p.m. of sweet peas and the like caused by *Erysiphe poligoni;* p.m. of herbaceous peonies, tree peonies and the like caused by *Erysiphe aquiagiae;* p.m. of ilexes, chinquapins, various oaks and the like caused by *Erysiphe heraclei;* p.m. of grapes caused by *Uncinula necator;* p.m. of crape myrtles caused by *Uncinula australiana;* p.m. of maples and the like caused by *Sawadaea tulasnei;* p.m. of oaks and the like caused by *Cystotheca wrightii;* p.m. of roses caused by *Sphaerotheca pannosa;* p.m. of apples caused by *Podosphaera leucotricha;* p.m. of persimmon caused by *Phillactinia kakicola;* p.m. of mulberries caused by *Phillactinia moricola;* and the like.

In applying the present germicide to the above diseases, the application season, concentration, number of treatment should be determined in accordance with the kind of germ attacking and the plant attacked. Generally, the earlier application the better the effect in therapy or in prevention. The germicidal composition may be repeatedly applied if necessary.

An optimum concentration for the dilutions in use is usually in the range of about 100 to 5000 ppm, though it should be determined according to the disease, plant attacked, and stage of the disease. A preferred concentration is about 200 to 3000 ppm for apple canker and about 1500 to 5000 ppm for powdery mildews. Since the germicidal composition is relatively harmless to plants, the concentration can be widely selected.

Optimum application season and application time also depend on the disease and plants. When symptoms appear, generally the earlier the application the better the results in both therapy and in prevention. The application may be repeated several times, if necessary. When the germicidal composition is applied to apple canker, a combination of high concentration applications during the tree's green age before budding, and further applications after harvest is advisable, though year round application also gives good results. For powdery mildews, weekly application is preferable.

The invention's germicidal composition may be used with other germicides such as Benomyl, Thiophanate-methyl, Morestan (6-Methylquinoxaline-2,3-dithiocarbonate), Thiophanate (1,2-bis(3-ethylcarbonyl-2-thioureido)), CECA (N-($\beta$-cyanoethyl)-chloroacetamide), DBEDC (Cu-complex of bis ethylenediamine dodecylbenzene sulfonate) and the like. It may also be applied alternately with other germicidal compositions to prevent the disease from acquiring a tolerance.

The 2-(2-hydroxyethylamino)-3-benzoylpropionates or salts thereof of the present invention have excellent efficacy for agricultural and horticultural plants diseases such as apple canker, powdery mildew of various kinds of plants and the like, and cause little damage, such as chlorosis of leaf, chlorosis of vein, withering of growing point etc, to the plants, but also have an extremely weak toxicity to man and beast (e.g., $LD_{50}$ of the ethylester is 7.6 g/Kg for a mouse and 4.79 g/Kg for a rat).

The effects of the invention's germicidal composition are further explained by the following examples.

EXAMPLE 1-15

Ethyl 2-(2-hydroxyethylamino)-3-benzoylpropionate hydrochloride was added to potato dextrose-agar culture medium in the concentration indicated in Table 1 and the suspensions of various kinds of germs were dropped on the culture medium. After incubation of the germs for two weeks in thermostat (25° C.), the growing conditions were observed.

The results are shown in Table 1. In Table 1, +++, ++, + and − represent "extremely much growth", "much growth", "a little growth" and "no growth" respectively.

TABLE 1

|  |  | Concentration of ethyl 2-(2-hydroxyethylamino)-3-benzoylpropionate hydrochloride (ppm) | | | | | |
|---|---|---|---|---|---|---|---|
| Ex. | Germs | 0 | 10 | 20 | 50 | 100 | 200 |
| 1 | *Valsa ceratosperma* | +++ | − | − | − | − | − |
| 2 | *Verticillium alboatrum* | +++ | +++ | ++ | − | − | − |
| 3 | *Botrytis alli* | +++ | + | − | − | − | − |
| 4 | *Cladosporium cucumerium* | +++ | +++ | +++ | − | − | − |
| 5 | *Cladosporium fulvum* | +++ | ++ | − | − | − | − |
| 6 | *Alternaria solani* | +++ | ++ | − | − | − | − |

TABLE 1-continued

| | | Concentration of ethyl 2-(2-hydroxyethylamino)-3-benzoylpropionate hydrochloride (ppm) | | | | | |
|---|---|---|---|---|---|---|---|
| Ex. | Germs | 0 | 10 | 20 | 50 | 100 | 200 |
| 7 | Stemphylium lycopersici | +++ | + | + | — | — | — |
| 8 | Fusarium oxysporum f. lycopersici | +++ | +++ | ++ | — | — | — |
| 9 | Colletotrichum lagenarium[1] | +++ | +++ | — | — | — | — |
| 10 | Colletotrichum lagenarium[2] | +++ | ++ | ++ | — | — | — |
| 11 | Phomopsis vexans | +++ | + | — | — | — | — |
| 12 | Sclerotinia sclerotiorum | +++ | +++ | +++ | — | — | — |
| 13 | Mycosphaerella melonis | +++ | +++ | — | — | — | — |
| 14 | Pyrenochaeta sp. | +++ | ++ | ++ | — | — | — |
| 15 | Cercospora kikuchii | +++ | + | — | — | — | — |

[1]Germ of anthracnose on cucumbers
[2]Germ of anthracnose on watermelons

EXAMPLE 16

Branches of Delicious apple (branch diameter: about 1 cm. thick) grown for 1-2 years were cut to 10 cm. length. The cut branches were dried in a low temperature chamber (3° C.) until the water content of the cut branches became 50%. The dried cut branches were immersed in an aqueous solution of ethyl 2-(2-hydroxyethylamino)-3-benzoylpropionate hydrochloride (500 ppm, 1000 ppm and 2500 ppm) for one minute and then dried.

Each cut branch was end bored by a white heated 8 mm diameter cork borer. *Valsa ceratosperma*, previously cultured for four days on a potato dextrose-agar culture medium, was introduced into the branch by inoculating the branch with the *Valsa ceratosperma* containing culture by means of the sterilized cork borer. The branches prepared in this way were placed on wet filter paper spread in a polyethylene tray. The tray was inserted into a polyethylene bag which was sealed and then the bag was put into a thermostat (25° C.) for various controlled times.

After removal from the thermostat, the length of disease spots on each branch was measured. The results obtained are shown in Table 2.

A similar experiment for comparison was carried out using Benomyl, i.e. methyl-1-(buthylcarbamoyl)-2-benzimidazole carbamate as the germicide. The results of the comparative experiment and also a control experiment, in which the dried cut branches were not immersed in germicide (blank), are also shown in Table 2.

TABLE 2

| Germicides | | Length of disease spot (mm) | | |
|---|---|---|---|---|
| Kinds | activity (ppm) | after 3 days | after 5 days | after 7 days |
| Ethyl 2-(2-hydroxyethyl-amino)-3-benzoylpropionate hydrochloride | 500 | 0 | 0 | 0.2 |
| | 1000 | 0 | 0 | 0 |
| | 2500 | 0 | 0 | 0 |
| Methyl-1-(buthylcarbamoyl)-2-benzimidazolecarbamate | 500 | 1.0 | 1.0 | 1.8 |
| | 1000 | 0.5 | 0.5 | 1.0 |
| | 2500 | 0 | 0 | 0 |

TABLE 2-continued

| Germicides | | Length of disease spot (mm) | | |
|---|---|---|---|---|
| Kinds | activity (ppm) | after 3 days | after 5 days | after 7 days |
| No germicide (blank) | 0 | 4.0 | 9.5 | 17.1 |

EXAMPLE 17

The same experiment as in Example 16 was carried out except that the apple branches were treated with the germicides (1000 ppm) on the third day after the branches were inoculated with the germ. The lengths of disease spots on the third day (the inoculation day), fifth day and seventh day were 5.1 mm, 5.2 mm and 5.2 mm respectively.

EXAMPLE 18

The prevention effect for anthracnose on cucumber was investigated in the following manner.

An aqueous solution of ethyl 2-(2-hydroxyethylamino)-3-benzoylpropionate hydrochloride (2500 ppm and 5000 ppm) was sprayed on cucumber seedlings (bifoliate age) of Tokiwa Hikari No. 3 (p type) variety which were planted in sections of two rows of three.

After air-drying the seedlings, a spore suspention of *Colletotrichum lagenarium* was inoculated on the test seedlings by means of a glass sprayer. The inoculated seedlings were kept at 20°-22° C. for four days in the inoculation box, and then allowed to stand in a glass chamber.

The number of disease spots of anthracnose that appeared on the cucumber leaves was measured on the sixth day after spraying the germicidal aqueous solution. The number of spots can be used to calculate a prevention value. Using the number of spots that appeared per control leaf as a reference, the relative number per hundred of spots prevented by the experimental germicide is the prevention value. Thus a perfectly preventive germicide has a prevention value of 100 and the control has a prevention value of 0. The experimental results are shown in Table 3.

TABLE 3

| Items examined | | | | |
|---|---|---|---|---|
| Active concentration of the germicide solution (ppm) | Number of leaves examined | Percentage of leaves attacked with the disease (%) | Number of disease spots per leaf | Prevention value per leaf (perfect prevention = 100) | Germicidal damage to seedlings |
| 5000 | 12 | 91.7 | 2.92 | 87.6 | none |
| 2500 | 12 | 83.3 | 2.83 | 88.0 | none |

TABLE 3-continued

| Active concentration of the germicide solution (ppm) | Number of leaves examined | Percentage of leaves attacked with the disease (%) | Number of disease spots per leaf | Prevention value per leaf (perfect prevention = 100) | Germicidal damage to seedlings |
| --- | --- | --- | --- | --- | --- |
| no germicide (blank) | 12 | 100 | 23.50 | 0 | — |

EXAMPLE 19

The prevention effect for cucumber scab was examined in the following manner.

An aqueous solution of ethyl 2-(2-hydroxyethylamino)-3-benzoylpropionate hydrochloride (2500 ppm or 5000 ppm) was sprayed on cucumber seedlings (bifoliate age) of Tokiwa Hikari No. 3 (p type) variety which were planted in sections in two rows of three.

After air-drying the seedlings, a spore suspention of Cladosporium cucumerium was inoculated on the test seedlings by means of a glass sprayer. The inoculated seedlings were kept at 18°-20° C. for four days in an inoculation box and then allowed to stand in a glass chamber.

The leaf area on which scab spots appeared was measured on the eighth day after spraying the aqueous germicide solution. The spotted area is expressed as a prevention value. The experimental results are shown in Table 4.

TABLE 4

| Active concentration of the germicide solution (ppm) | Number of leaves examined | Percentage of leaves attacked with the disease (%) | Percentage of leaf area with disease spots (%) | Prevention value per leaf (Perfect prevention = 100) | Germicidal damage to seedlings |
| --- | --- | --- | --- | --- | --- |
| 5000 | 6 | 100 | 20.0 | 70.7 | none |
| 2500 | 6 | 100 | 25.0 | 63.4 | none |
| no germicide | 6 | 100 | 68.3 | 0 | — |

EXAMPLE 20

The prevention effect for powdery mildew on cucumbers caused by Sphaerotheca fuliginea was examined in the following manner.

Cucumber seedlings (bifoliate age) of Tokiwa Hikari No. 3 (p type) variety planted in sections of two rows of three were inoculated with the above germ by brushing on spores from a cucumber leaf attacked with powdery mildew.

An aqueous solutions of ethyl 2-(2-hydroxyethylamino)-3-benzoylpropionate hydrochloride (2500 ppm and 5000 ppm) were sprayed on the test plants on the third and ninth days after inoculation.

The leaf area on which powdery mildew spots appeared was measured on the fifteenth day after the seedlings were inoculated with the germ. The spotted area is expresses as a prevention value. The experimental results are shown in Table 5.

TABLE 5

| Active concentration of the germicide solution (ppm) | Number of leaves examined | Percentage of leaves attacked with the disease (%) | Percentage of leaf area with disease spots (%) | Prevention value per leaf (Perfect prevention = 100) | Germicidal damage to seedlings |
| --- | --- | --- | --- | --- | --- |
| 5000 | 18 | 0 | 0 | 100 | none |
| 2500 | 18 | 0 | 0 | 100 | none |
| 0 (blank) | 18 | 100 | 77.3 | 0 | — |

EXAMPLE 21

The same experiment as Example 20 was carried out except that isopropyl 2-(2-hydroxyethylamino)-3-benzoyl-propionate hydrochloride was used instead of ethyl 2-(2-hydroxyethylamino)-3-benzoylpropionate hydrochloride. The results obtained are shown in Table 6.

TABLE 6

| Active concentration of the germicide solution (ppm) | Number of leaves examined | Percentage of leaves attacked with the disease (%) | Percentage of leaf area with disease spots (%) | Prevention value per leaf (Perfect prevention = 100) | Germicidal damage to seedlings |
| --- | --- | --- | --- | --- | --- |
| 2500 | 18 | 0 | 0 | 100 | none |
| 2000 | 18 | 0 | 0 | 100 | none |

TABLE 6-continued

| Active concentration of the germicide solution (ppm) | Number of leaves examined | Percentage of leaves attacked with the disease (%) | Percentage of leaf area with disease spots (%) | Prevention value per leaf (Perfect prevention = 100) | Germicidal damage to seedlings |
|---|---|---|---|---|---|
| 1500 | 18 | 55.6 | 8.9 | 88.5 | none |
| 0(blank) | 18 | 100 | 77.3 | 0 | — |

EXAMPLE 22

The prevention effect for powdery mildew on strawberries caused by *Sphaerotheca humuli* was examined in the following manner.

Strawberry seedlings (3-4 leaves) of Danar variety dug up and planted in a pot in two row of three without drying the roots was inoculated with the above germ by brushing on the spores from a strawberry leaves attacked with powdery mildew.

An aqueous solution of sec-butyl 2-(2-hydroxyethylamino)-3-benzoylpropionate hydrochloride was sprayed on the test plant on the third and ninth days after the seedlings were inoculated with the germ.

The leaf area on which powdery mildew spots appeared was measured on the fifteenth day after the seedlings were inoculated with the germ. The spotted area is expressed as a prevention value. The results are shown in Table 7.

TABLE 7

| Active concentration of the germicide solution (ppm) | Number of leaves examined | Percentage of leaves attacked with the disease (%) | Percentage of leaf area with disease spots (%) | Prevention value per leaf (Perfect prevention = 100) | Germicidal damage to seedlings |
|---|---|---|---|---|---|
| 3000 | 20 | 0 | 0 | 100 | none |
| 2000 | 20 | 0 | 0 | 100 | none |
| 1000 | 20 | 83.3 | 46.1 | 40.4 | none |
| 0 (blank) | 20 | 100 | 77.3 | 0 | — |

EXAMPLE 23

The emulsion was prepared by blending 25 g of ethyl 2-(2-hydroxyethylamino)-3-benzoylpropionate, 25 ml of isopropanol, 3 g of Demol T (formalin condensed naphthalenesulfonate available from Kao Sekken Inc.), 2 g of Emal 10 (sodium lauryl sulphate available from Kao Sekken Inc.) and 45 g of water.

The prevention effect of the emulsion prepared above for powdery mildew on eggplants caused by *Erysiphe cichoracearum* was examined in the following manner.

Eggplant seedlings of Shinkitsushin variety planted in sections in two rows of three were inoculated with the above germ by brushing on spores from other eggplant leaf attacked with the powdery mildew.

An aqueous solution of ethyl 2-(2-hydroxyethylamino)-3-benzoylpropionate (2000 ppm and 2500 ppm) was sprayed on the test plant on the third or ninth days after the seedlings were inoculated with the germ by means of glass sprayer.

The leaf area on which powdery mildew spots appeared was measured on the fifteenth day after the seedlings were inoculated with the germ. The spotted area is expressed as a prevention value. The results obtained are shown in Table 8.

TABLE 8

| Active concentration of the germicide solution (ppm) | Number of leaves examined | Percentage of leaves attacked with the disease (%) | Percentage of leaf area with disease spots (%) | Prevention value per leaf (Perfect prevention = 100) | Germicidal damage to seedlings |
|---|---|---|---|---|---|
| 2500 | 18 | 0 | 0 | 100 | none |
| 2000 | 18 | 0 | 0 | 100 | none |
| 0 (blank) | 18 | 100 | 77.3 | 0 | — |

What is claimed is:

1. A germicidal composition for agriculture and horticulture which comprises as an active ingredient a germicidally effective amount of a 2-(2-hydroxyethylamino)-3-benzoylpropionate or a salt thereof represented by the general formula:

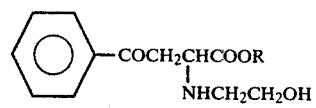

wherein R a is lower alkyl group, and agriculturally acceptable adjuvants therefor.

2. The germicidal composition according to claim 1, wherein alkyl group is selected from the group consisting of ethyl, propy, isopropyl and sec-butyl group.

3. The germicidal composition according to claim 1, wherein the salt is a hydrochloride.

4. The germicidal composition according to claim 1, wherein it is in the form of water soluble powder, emulsifiable concentrate or wettable powder.

5. The method of controlling apple cankers and powdery mildews in plants comprising applying to said plants a germicidally effective amount of a 2-(2-hydroxyethylamino)-3-benzoylpropionate or a salt thereof represented by the general formula:

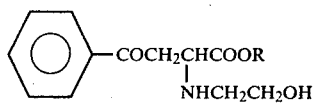

wherein R is lower alkyl.

6. The method according to claim 5, wherein R is selected from the group consisting of ethyl, propyl, isopropyl and sec-butyl.

7. The method according to claim 5, wherein the salt is a hydrochloride.

* * * * *